(12) United States Patent
Rijcken et al.

(10) Patent No.: US 9,339,554 B2
(45) Date of Patent: May 17, 2016

(54) TUNABLE, BIODEGRADABLE LINKER MOLECULES FOR TRANSIENT CONJUGATION OF COMPONENTS IN DRUG DELIVERY SYSTEMS, AND DRUG DELIVERY SYSTEMS PREPARED THEREWITH

(75) Inventors: Cristianne Johanna Ferdinand Rijcken, Utrecht (NL); Wilhelmus Everhardus Hennink, Utrecht (NL); Cornelis Franciscus van Nostrum, Utrecht (NL); Isil Altintas, Utrecht (NL); Steffen van der Wal, Utrecht (NL); Robertus Matthias Joseph Liskamp, Utrecht (NL); Johannes Anna Wilhelmus Kruijtzer, Utrecht (NL)

(73) Assignee: CRISTAL DELIVERY B.V., Utrecht (NL)

( * ) Notice: Subject to any disclaimer, the term of this patent is extended or adjusted under 35 U.S.C. 154(b) by 6 days.

(21) Appl. No.: 13/825,036

(22) PCT Filed: Jul. 14, 2011

(86) PCT No.: PCT/NL2011/050509
§ 371 (c)(1),
(2), (4) Date: May 9, 2013

(87) PCT Pub. No.: WO2012/039602
PCT Pub. Date: Mar. 29, 2012

(65) Prior Publication Data
US 2013/0261094 A1    Oct. 3, 2013

Related U.S. Application Data

(60) Provisional application No. 61/384,730, filed on Sep. 21, 2010.

(51) Int. Cl.
*A61K 47/48* (2006.01)
*C07C 323/52* (2006.01)

(52) U.S. Cl.
CPC ......... *A61K 47/48038* (2013.01); *A61K 47/488* (2013.01); *A61K 47/48176* (2013.01); *A61K 47/48215* (2013.01); *C07C 323/52* (2013.01)

(58) Field of Classification Search
CPC ........... A61K 47/488; A61K 47/48038; A61K 47/48215; C07C 323/52
See application file for complete search history.

(56) References Cited

U.S. PATENT DOCUMENTS 2,496,275 A * 2/1950 Dickey ................ C08F 18/22
                                                    526/288
3,220,986 A * 11/1965 Harris ................ C07C 323/00
                                                    526/271
4,171,324 A * 10/1979 Muller et al. ............. 562/120
5,457,172 A * 10/1995 Curci ................ C07C 69/675
                                                    526/240
5,935,599 A * 8/1999 Dadey ................ A61K 9/1273
                                                    264/4.1
6,506,804 B2 * 1/2003 Schultz ...................... 516/59
2009/0246211 A1 * 10/2009 Henri et al. ............. 424/181.1

FOREIGN PATENT DOCUMENTS

WO    2010/033022 A1    3/2010

OTHER PUBLICATIONS

Read et al (Journal of Biological Chemistry, 1961, vol. 237, pp. 1521-1522).*
Campolmi et al, Immediate and delayed sensitization to garlic, 1982, Contact Dermatitis, vol. 8, pp. 352-353.*
Bae et al (Macromolecules, 2009 (web date—Apr. 2009), vol. 42, pp. 3437-3442).*
Deng et al (Nano Today, 2012, vol. 7, pp. 467-480).*
Talelli et al (Nano Today, 2015, article in press, pp. 1-25).*
Crielaard et al (Angewandte Communications, published online on Jun. 12, 2012, vol. 51, pp. 7254-7258).*
Fang et al (Expert Opinions in Drug Delivery, 2012, vol. 9, pp. 657-669).*
Bae et al., "Vinyl Sulfone-Terminated PEG-PLLA Diblock Copolymer for Thiol-Reactive Polymeric Micelle," Macromolecules, 42:3437-3442, 2009.
Curci et al., "Synthesis of Functionalized Acrylates," Organic Preparations and Procedures Int., 25:649-657, 1993.
Kaleas et al., "Industrial Case Study: Evaluation of a Mixed-Mode Resin for Selective Capture of a Human Growth Factor Recombinantly Expressed in *E coli*," Journal of Chromatography, 1217:235-242, 2010.
Morales-Sanfrutos et al., "Vinyl Sulfone: A Versatile Function for Simple Bioconjugation and Immobilization," Organic & Biomolecular Chemistry, 8:667-675, 2010.
International Search Report dated Feb. 3, 2012 for International Application No. PCT/NL2011/050509.

* cited by examiner

*Primary Examiner* — Sean Basquill
*Assistant Examiner* — Mark V Stevens
(74) *Attorney, Agent, or Firm* — Morrison & Foerster LLP

(57) ABSTRACT

The present invention relates to a particular class of biodegradable linkers, ensuring transiently stable conjugation of building blocks and/or bioactive compounds into drug delivery systems (DDS), such as DDS based on polymeric micelles or hydrogels. In addition, the present invention relates to compounds, comprising said linkers, such compounds preferably being prodrugs. Further, the invention is directed to the use of said linkers, and especially said biodegradable linkers, in a drug delivery system. Moreover, the invention relates to controlled release system comprising a polymer matrix, capable of releasing an active ingredient, wherein the active ingredient is covalently linked to the polymer molecules of the polymer matrix through said linkers, as well as to a method of synthesizing these linkers and preparing such controlled release systems.

14 Claims, 5 Drawing Sheets

TUNABLE, BIODEGRADABLE LINKER MOLECULES FOR TRANSIENT CONJUGATION OF COMPONENTS IN DRUG DELIVERY SYSTEMS, AND DRUG DELIVERY SYSTEMS PREPARED THEREWITH

RELATED APPLICATIONS

This application is the U.S. National Stage of International Application No. PCT/NL2011/050509, filed Jul. 14, 2011, published in English, and claims the benefit of U.S. Provisional Application No. 61/384,730, filed on Sep. 21, 2010, the entire teachings of the above applications are incorporated herein by reference.

The present invention relates to a particular class of biodegradable linkers, ensuring transiently stable conjugation of building blocks and/or bioactive compounds into drug delivery systems (DDS), such as DDS based on polymeric micelles or hydrogels. In addition, the present invention relates to compounds, comprising said linkers, such compounds preferably being prodrugs. Further, the invention is directed to preparation methods for and the use of said linkers, and especially said biodegradable linkers, in a drug delivery system. Moreover, the invention relates to controlled release system comprising a polymer matrix, capable of releasing an active ingredient, wherein the active ingredient is covalently linked to the polymer molecules of the polymer matrix through said linkers, as well as to a method of preparing such controlled release systems.

The delivery of bioactive compounds to patients is often hampered by a poor solubility, rapid clearance, occurrence of high toxicity, or combinations thereof. These issues can be alleviated by entrapment of bioactive compounds in suitable drug delivery systems.

DDS, such as polymeric micelles and hydrogel systems, are considered as promising candidates for the targeted delivery of drugs or other suitable bioactive compounds. For example, polymeric micelles based on biodegradable thermosensitive polyhydroxypropyl- or polyhydroxyethyl-methacrylamide lactates, can encapsulate a large variety of hydrophobic therapeutic compounds. Such systems are for instance described in WO-01/09198 and WO-2005/087825. Particularly, said latter document for example describes micelles based on hydrophobically modified PEG-polymethacrylamide block copolymers in detail. The polymers described in both WO publications display a unique combination of temperature sensitivity and biodegradability, which provide easy drug loading and controlled release properties, respectively, to the delivery systems prepared therefrom.

These and various other, preferably, nano-sized particles are currently evaluated in the search for drug carrier systems that selectively target sites of disease. This targeted delivery aims at improving therapeutic efficacy and simultaneously decreasing the toxicity profiles of encapsulated compounds.

Without wishing to be bound to a particular theory, it is considered necessary or at least desirable that drug carrier systems of the type of the present invention form a long circulating system in the blood stream and release in a controlled manner the active ingredients present therein. That is, a need exists for depot systems which lead—after one application—to therapeutic levels of active ingredients over a longer period of time than achievable when using the free active ingredient. With such systems, it is an important advantage when the release is tuneable; for instance dependent on the type of active ingredient, release rate and specific (medical) indication.

In case diseases or disorders are associated with or accompanied by vesicular irregularities a long circulation will likely lead to an increased take up of the drug delivery system and the release therefrom of active ingredients. In this light, it is noted that leaky vessels and dysfunctional lymphatic drainage during inflammation and tumour growth provide, for example, a gateway for access of nanoparticles after intravenous administration. This so-called enhanced permeation and retention (EPR) effect allows the accumulated nanocarriers to release drugs in the vicinity of diseased cells. Critical aspect of this strategy is a long-circulatory half-life of the nanocarrier to increase the statistical probability of extravasation.

The desired long-circulating characteristic can, e.g., be achieved by a dense hydrophilic coating of a nanoparticle to prevent scavenging by the host immune system. In this respect, liposomes covered with a polyethylene glycol (PEG) coating are considered as the golden standard as these display circulation half lives of around 8-12 hours and up to 5-10% of the injected dose accumulates in diseased areas.

Obviously, an enhanced drug concentration in the targeted region can only be achieved if encapsulated drug molecules stay associated until the carrier reaches the target site. In said search for drug carrier systems, it was found that the systems evaluated can be improved in long circulation times and accumulation in for instance tumour tissue by covalent coupling of active ingredients to the delivery system.

Particularly, Rijcken et al. described in an article titled "Hydrolysable core-crosslinked thermosensitive polymeric micelles: synthesis, characterisation and in vivo studies" in Biomaterials 2007, 28, 5581-5593 that it was demonstrated that cross-linking, i.e. the covalent conjugation of hydrophobially modified PEG-polymethacrylamide block copolymers in a micellar core, realises a long blood circulation after intravenous administration in mice. In addition, it was found that empty cross-linked micelles accumulate to a 6-fold higher extent in tumour tissue when compared with non-cross-linked micelles.

However, non-covalent entrapment of drug compounds in these crosslinked micellar cores could not prevent a rapid release of the drug molecules immediately after injection. In WO-2010/033022, it was demonstrated that by covalent entrapment of drug molecules in the micellar core, the drugs can really benefit from the prolonged circulation which consequently elevated drug concentrations in tumour tissue Particularly, data on a 25-fold elevated drug concentration in case of a subcuteanous model were found.

The present invention improves these known systems (as will be illustrated herein-below for, for instance, paclitaxel (PTX) and dexamethasone (DMS); it is however emphasized that the present invention is applicable to various active ingredients, including drugs, and hence applicable in the treatment of all kinds of diseases and indications). Such systems may be applied using any kind of known techniques, such as by intravenous administration or implantation. This will ensure improved target tissue selectivity for e.g. polymeric micelles and hydrogels.

More in detail, the drug has to be released in time to be able to exert its therapeutic effect. By using a biodegradable linkage, the original drug molecule will be released according to a specific controlled release profile. The present invention aims at the intravenous administration of DDS, such as micellar delivery vehicles, which subsequently stay long in the blood circulation and release under these physiological conditions (pH 7.4) the entrapped drugs according to a predefined rate. Hence, there is a need to develop novel covalent drug linkers, which hydrolyse for example within 24-48 hours under physiological conditions, thereby releasing the original drug compound according to a controlled manner. This tuneablility requires tuneablility in either drug (or another bioactive material), linker and/or polymer chemical conjugation. Moreover, molecules that are to be used in drug delivery systems need to be inherently safe and cause no short or long toxicity issues.

The invention concerns a novel class of biodegradable linkers that ensures the transiently stable conjugation of building blocks and/or bioactive compounds into drug delivery systems (DDS, for example polymeric micelles or hydrogels). In this description, "building blocks" are components used to (self-)assemble into a drug delivery system, either being of natural or synthetic origin, potentially (partially) derivatised with reactive moieties. Well-known examples include lipids, cholesterol, various possible polymers (e.g., PLGA, PLA, chitosan). In this description "bioactive compounds" are compounds either from natural or synthetic origin, that can exert a preventive and/or therapeutic effect in the body, that are used to visualise particular organs/pathways in vivo, or a combination of both.

BRIEF DESCRIPTION OF DRAWINGS

FIG. 6a shows the results for taxol, FIG. 6b shows the results for various linked forms of paclitaxel, and FIG. 6c shows both entrapped and released paclitaxel.

Figure 1:
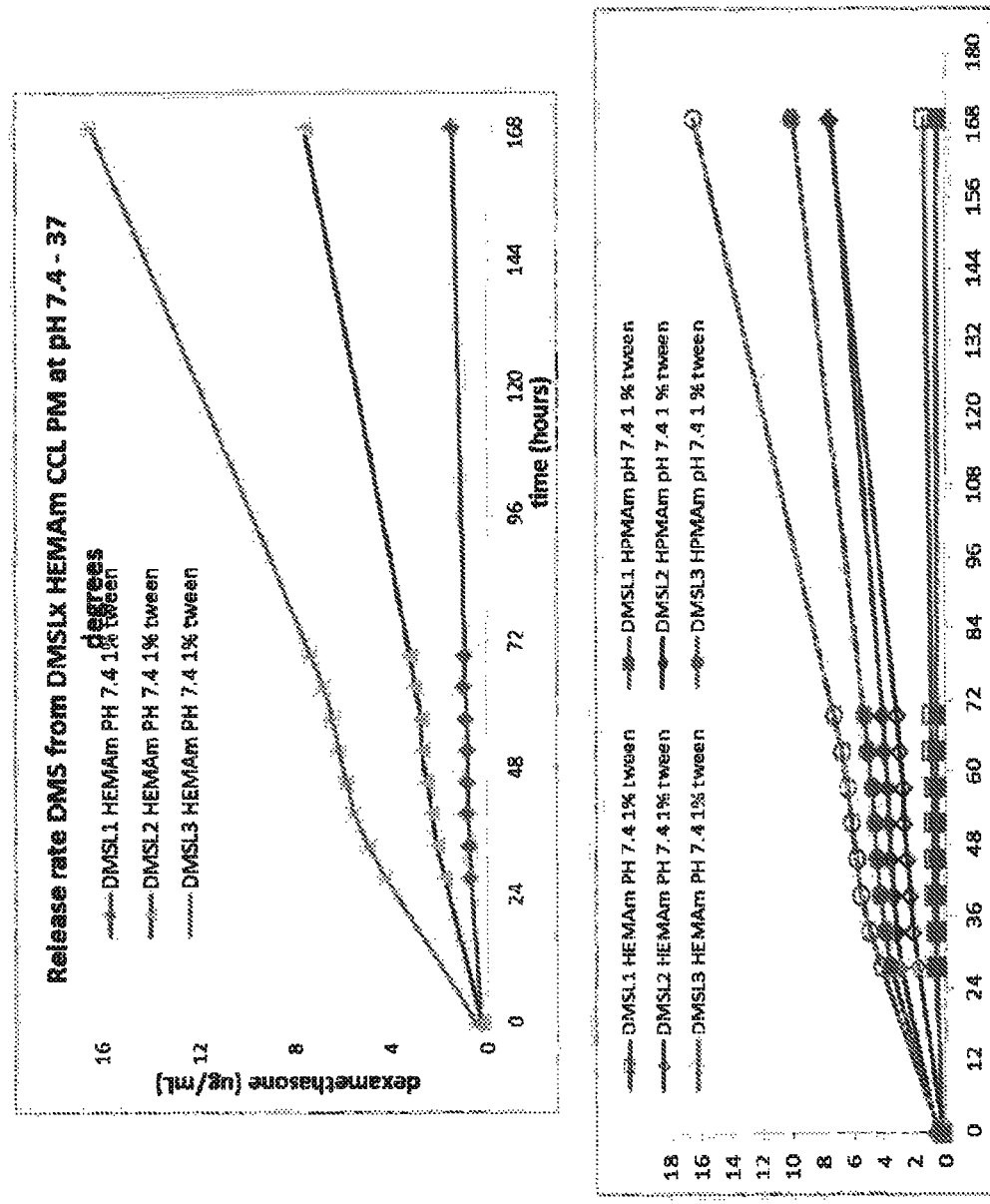
FIG. 1 is a pair of graphs showing the release rate of dexamethasone prodrug from core-crosslinked polymeric micelles as a function of the linker used to couple DMS to the polymer.

Particularly, in a first aspect, the present invention relates to a linker comprising (i) an OH-containing moiety, preferably a hydroxyl group or a carboxylic acid moiety, or an NH-containing moiety such as an amino group or a substituted NH-group, wherein the substituent is a $C_1$-$C_3$ alkyl group; (ii) a dialkylated sulfur atom; and (iii) a conjugation moiety. These linkers are biodegradable under physiological conditions.

More specifically, an important feature of these linkers is that the linkages of the entrapped compounds or drug delivery systems components are subsequently hydrolysed, thus resulting in release of the compounds and/or destabilisation of the DDS. The corresponding hydrolysis kinetics are tuneable by modifying the type of linker.

In a preferred embodiment, the linker comprises an OH-containing moiety such as a carboxylic acid, a derivatised dialkylated sulfur atom and a conjugation moiety. Such a linker can be exemplified by the following formula:

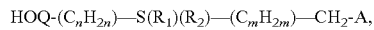

HOQ-($C_nH_{2n}$)—S($R_1$)($R_2$)—($C_mH_{2m}$)—$CH_2$-A, wherein n and m are integers from 0 to 20, and preferably from 1 to 10. In preferred embodiments, n is an integer from 1-5, more preferably from 1-3; and m is an integer from 1-7; more preferably from 1-5;

wherein $R_1$ and $R_2$ are independently from each other selected from an electron lone pair, an oxygen moiety, such as =O, a nitrogen moiety, such as =N—$R_x$, wherein $R_x$ is a homo- or heterogenous group of atoms, and preferably, independently, a straight or branched $C_1$-$C_6$ alkyl, a straight or branched $C_2$-$C_6$ alkenyl, which alkyl or alkenyl group may optionally be substituted by one or more halogen groups, hydroxyl groups, amino or substituted amino groups, carboxylic acid groups, nitro groups or cyano groups; or aromatic groups, and preferably a phenyl group optionally be substituted by one or more of the substituents mentioned for the alkyl and alkenyl groups; or a halogen group, a hydroxyl group, an amino group, or a substituted amino group (the substituents being one or two $C_1$-$C_3$ alkyl groups), a carboxylic acid group, a nitro group, or a cyano group;

wherein A is a conjunction moiety; and wherein Q is a direct bond, a C=O, a C=NH or C=$NR_p$ group, wherein $R_p$ is a $C_1$-$C_3$ alkyl. In this formula the HO-Q group can be replaced by a $HR_9NQ$ group, wherein $R_9$ can either be a hydrogen atom or a $C_1$-$C_3$ alkyl group.

In the following formula, the HO-Q group is a carboxylic acid group and the conjugation moiety A is a polymerisable methacrylate, which moieties are also exemplified in the working examples herein-below:

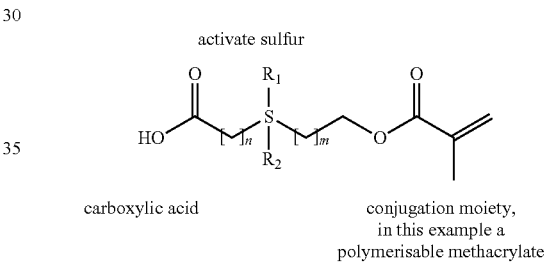

activate sulfur carboxylic acid              conjugation moiety,
                             in this example a
                             polymerisable methacrylate Suitable conjugation groups are polymerisable moieties of the formula —$P_L$—$R_V$C=$CR_U R_W$, wherein —$P_L$— is a linking group such as an —O—, a —NH—, a substituted

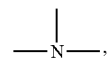

the substituent being a $C_1$-$C_3$ alkyl, an —O—C(O)—, an —O—(C(O))$_r$—$C_bH_{2b}$, wherein r is 0 or 1, and b is an integer from 1 to 6; and $R_U$, $R_V$ and $R_W$, independently, represent a hydrogen atom or a $C_1$-$C_3$ group.

Premature release of drugs or other bioactive components from cross-linked micelles is overcome by the covalent fixation of encapsulated prodrugs via a biodegradable linkage to the micellar core in the cross-linking step. To allow covalent incorporation of the prodrug in the polymer network upon crosslinking of the micellar core and controlled release, for instance, a polymerisable methacrylate group is attached to the drug using various hydrolytically sensitive linkers. The latter are specifically designed to be able to fine-tune the release rate of the drug from the micelles. More specifically, hydroxyethylmethacrylate is conjugated to the drug molecule, for example the model drug DMS, which is easily to modify and has a proven antitumour effect, via a sulphide (DMSL1), a sulphoxide (DMSL2), and sulphone (DMSL3)

ester. The increasing oxidation degree of the sulphur atom increases its electron withdrawing character and thereby increases the rate of hydrolysis of the neighbouring ester bond. Hence, it was found that these linkers are not only biodegradable but also bring large flexibility to the invention.

In other words, the type of derivatisation of the sulfur atom has a pronounced effect. Particularly, it was realized that different oxidation states of sulfur can be attained and used to primarily determine the stability of the nearby ester by in- or decreasing electron density of the ester carbonyl atom. Importantly, the type of derivatisation of the sulphur atom enables further fine-tuning or destabilising effects. Further modifications can be made using different substituents on the sulfur atom, of which examples of nitrogen and oxygen containing moieties are shown below. Additional derivatisation on the nitrogen atoms, for example, further enables further fine-tuning or destabilising effects. Moreover, sulfur containing linkers containing less than two free electron pairs have the potential to be chiral. Typical examples, including but not limited to, are shown in the following table:

| Bruto formula | Chemical name substituent | Chemical structure substituent | Abbreviated name |
|---|---|---|---|
| S | sulphide |  | L1 |
| SO | sulphoxide |  | L2 |
| SO$_2$ | sulphone |  | L3 |
| S(O)NR | sulfoximine | 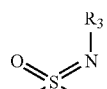 | L4 |
| S(NR$_1$)(NR$_2$) | sulfone diimine | 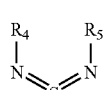 | L5 |
| S(NR) | sulfilimine |  | L6 |

In this table, R$_3$-R$_4$ independently have the meaning of a hydrogen atom, a C$_1$-C$_3$ alkyl group or of other moieties with general electron pushing or donating properties, e.g. a halogen substituent such as a fluor substituent or an alkyne moiety. Further, the position of the (derivatised) sulfur atom in the linker relative to the carboxylic acid moiety (indicated as n in the formulae herein-above) and the position of the (derivatised) sulfur atom in the linker relative to the conjugation moiety A (indicated as m in the formulae herein-above), can be used to influence the biodegradability of the linker and the release of the active constituent.

These indicated variables mentioned above do not require each time chemical optimisation of the ester bond formation, but a single conjugation method of a drug/building block to a linker molecule can be used. The linkers of the invention based on dialkylated sulfur potentially further derivatised with electron withdrawing or donating moieties in the proximity of an ester bond, an ether bond or an amide bond for controlled drug delivery purposes, can be used to affect (de)activation of the said bond's hydrolytical sensitivity by a nearby sulfur-derivative; are able to tailor the hydrolysis sensitivity of said bond for controlled drug delivery purposes; and cover a wide time span with respect to hydrolysis rate.

In preferred embodiments, the invention relates to compounds comprising said linker coupled through its COOH group to dexamethasone or paclitaxel. Alternatively, the linker could contain a (primary or secondary) OH moiety and the drug a COOH moiety. However, the present invention is not limited to these active components; the type of bioactive compound to be entrapped, includes but is not limited to, drug molecules, for example of the (gluco)corticosteroid type or of the chemostatic type, peptides/proteins, imaging agents, genetic material or a combination of these.

In a second aspect, the present invention relates to the use of the compounds according to said first aspect as linker, and especially as biodegradable linker, in a drug delivery system. Particularly, these compounds are used as biodegradable linker, wherein the linker is biodegradable under physiological conditions. "Physiological conditions" are conditions present in an organism to be treated with the DDS of the invention; for humans these conditions encompass a pH of about 7.4 and a temperature of about 37° C. This linker is present between the carrier molecules and the active ingredient; that is, the active ingredient is covalently coupled to the matrix material and is hence part of a core-cross-linked system. Suitable active ingredients are drug molecules, for example of the (gluco)corticosteroid type or of the chemostatic type, peptides/proteins, imaging agents, genetic material or a combination of these. In a preferred embodiment of this use, the drug delivery system releases dexamethasone or paclitaxel as active ingredient.

In order to synthesize and form a DDS, comprising and releasing active ingredients, using the linker molecules of the invention, it is a requirement to have available a functional moiety on the building block and/or bioactive compound to enable conjugation to the linker. This functional, reactive moiety on the building block or bioactive compound can be chosen by the skilled person on the basis of his common chemical knowledge and may for example be a primary or secondary alcohol or amine or a COOH group. In a preferred embodiment, this is a primary or secondary alcohol, or COOH.

In a subsequent step, a conjugation between the carboxylic acid moiety of the linker and, for example, the alcohol moiety of the building block or bioactive compound is initiated, thereby forming an ester bond, which conjugation is exemplified by the following reaction scheme:

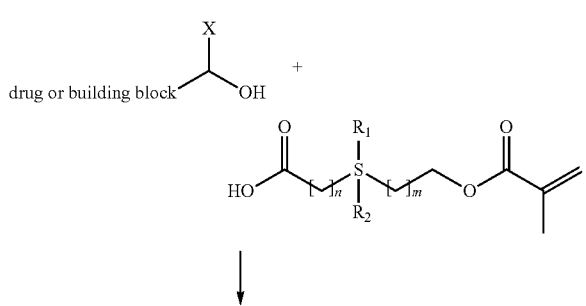

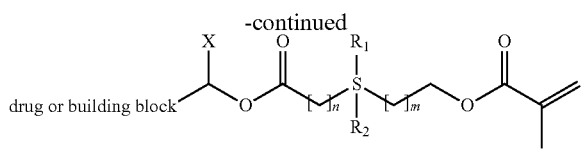

In this scheme, X may, e.g., be H or CH$_3$ and R$_1$ and R$_2$ have the above-given meaning. Preferably, R$_1$ and R$_2$ are not at the same time H.

Resulting from the above-described general conjugation, a prodrug or modified building block is obtained as further aspect of the present invention.

This prodrug or modified building block is subsequently (stepwise) entrapped in and conjugated to a DDS. This type of conjugation, includes but is not limited to, a condensation reaction (e.g. carboxylic acid and an alcohol moiety), a (free radical) polymerisation reaction, a click reaction and similar ways to conjugate the (derivatised) linker to a polymeric system. The formed bond is—in accordance with a further aspect of the present invention—in time hydrolysed with a tunable rate as described herein-below in further detail.

Either the drug, the building block or both the bioactive agent and the building block of the delivery system components can be covalently linked to each other via above described class of linkers.

These steps are in conformity with the method forming the invention of WO-2010/033022, which document is incorporated herein by reference for providing a detailed preparation method of the DDS of the present invention.

Hence, the polymerisable drugs or prodrugs of the invention are incorporated into the core of DDS, such as micelles, in a two-step process. First, the hydrophobic drug conjugates were physically entrapped in the hydrophobic core upon, e.g., micelle formation. Secondly, polymers were cross-linked in the micellar core by free radical polymerisation and the (pro) drugs were simultaneously co-polymerised in the newly formed intertwined network. In accordance with the invention, a highly efficient encapsulation of the prodrugs (>95%) was obtained at a loading capacity of 10% (w/w final drug/polymer concentrations). As observed by dynamic light scattering, the resulting micelles were rather monodisperse with a size of ~60-90 nm (polydispersity index less than 0.1).

Hence, a further aspect of the present invention is a controlled release system comprising a polymer matrix, capable of releasing an active ingredient, wherein the active ingredient is covalently linked to the polymer molecules of the polymer matrix through a linker of the invention.

The use of the class of linkers of the present invention is not limited to the use of polymers that can form micelles: it also allows for the biodegradable entrapment of (drug) molecules in polymeric nanoparticles, microspheres, hydrogels or coatings or similar DDS known to somebody skilled in the art.

With regard to the application of these (drug-loaded) delivery systems, non-limiting examples are (i) controlled release of (drug) molecules entrapped in (crosslinked) micelles upon administration in vivo, e.g. by oral application, injection in the blood stream, or by direct injection in an organ or tumour; (ii) controlled release of drugs and/or proteins entrapped in a (crosslinked) polymeric hydrogel, either upon intravenous administration (nanogels) or upon localised administration (macrogels); and (iii) controlled release of (drug) molecules upon coating of a device with entrapped drug molecules.

In yet a further aspect, the present invention is directed to methods for preparing the linkers of the invention. In a first embodiment of this aspect an alkyl bromoacetate is reacted with a mercaptoalcohol; the resulting alcohol is subsequently reacted with the A-Cl, wherein A is the conjugation moiety; and splitting of the alkyl group.

In a further embodiment, the product obtained is further oxidized, for example using sodiumperiodate.

In yet a further embodiment, an alkylbromoantax is reacted with a mercaptoalcohol, followed by fully oxidizing the sulfur atom, reacting the resulting alcohol with A-Cl, wherein A is the conjugation moiety and splitting of the alkyl group.

These methods are illustrated in all detail in Example 1.

Yet another aspect of the invention is a method of preparing such a controlled release system, comprising the steps of providing a building block and/or bioactive compound having a functional moiety to enable conjugation to the linker, preferably a primary or secondary alcohol or a COOH; initiating a conjugation between the —OH containing or the —NH containing moiety, such as the carboxylic acid moiety of the linker and said functional moiety of the building block or bioactive compound, thereby forming a prodrug or modified building block; and entrapping in and conjugating to the polymer matrix of said prodrug or modified building block.

Because of the formed linkage present between the polymer matrix and the active ingredient (drug, building block) such as an ester linkage, the controlled release system formed is subject to a controlled degradation and release. Particularly, the linkage, and especially the ester linkage, hydrolyses at physiological conditions in time.

As sketched herein-above, an important aspect of the present invention is that the moiety in proximity of the hydrolysable group, such as the ester group (=substituent) in the linker retards or facilitates (ester)hydrolysis. Molecularly spoken, the substituent is a sulfur atom, which can be positioned closer to or further from the hydrolysable linkage (reflected by the meaning of n in the formula shown hereinabove) to reduce or enhance (ester) stability, respectively, and which is further activated by derivatisation with electron withdrawing moieties, or deactivated by derivatisation with electron donating moieties. In other words, the choice and position of said substituent enables a real fine-tuning towards a desired hydrolysis rate. The practical consequence is that release of the (original) drug molecule and/or disintegration of the DDS is occurring according to a rate which is truly controlled by the type and position of the substituent.

The concept of the present invention will be exemplified by (but is not limited to) polymeric micelles based on biodegradable thermosensitive polyhydroxypropyl- or polyhydroxyethyl-methacrylamide lactates. To ensure long circulation and tumour accumulation, these micelles are core-crosslinked. To limit rapid elimination of the encapsulated drugs after introduction in the body to be treated, e.g., by injection in the body, such as by intravenous administration and/or to increase target tissue selectivity, the linkers of the present invention are used.

This type of polymeric micelles can encapsulate a large variety of (slightly) hydrophobic therapeutic compounds. Herein-below, dexamethasone (DMS) and paclitaxel (PTX) will be used as illustrative active components.

It will be shown that a novel class of DMS- and PTX prodrugs can be covalently incorporated in the network of the cross-linked micelles and show a really controlled release in vitro (between days and weeks).

With a very long half-life in the circulation of 14 hr as compared to 0.09 hr for the free drug and 0.12 hr for non-covalently encapsulated DMS, it is demonstrated that the covalent linkage of prodrugs to CCL micelles prevents premature burst release in the blood stream. The circulation half-life is even clearly longer than dexamethasone phosphate (DMS-P) in sterically stabilised liposomes (i.e. 7.6 hr), which is considered to be the golden standard at present. As a result, the co-cross-linked prodrug provides significantly enhanced tumour accumulation (23-fold higher than for the free drug). Therapeutic efficacy was demonstrated by a similar delay in subcutaneous melanoma tumour growth as compared to free DSM-P.

Particularly, polymeric micelles based on bioresorbable polymers, being thermosensitive poly(N-hydroxyalkyl-methacrylamide) derivatised with oligolactate side chains are developed. These block copolymers with a thermosensitive block and a PEG-block are completely water soluble at 0° C., but rapidly self-assemble into small monodisperse micelles of ~70 nm upon heating above the, tuneable, phase transition temperature. This method is applied to encapsulate a large variety of hydrophobic drugs, almost quantitatively, within the micellar cores.

As described above, the stability of such micelles was already enhanced by covalent cross-linking of the block copolymers after modifying the thermosensitive block with polymerisable methacrylate groups. The resulting core-crosslinked micelles displayed an excellent stability in vitro while fully retaining their biodegradability. Most importantly, cross-linking the micelles was critical to achieve a long blood circulation (half-life of 13 hours) in mice and a high, sustained tumour accumulation The present invention avoids—after intravenous administration of the drug-loaded micelles—a too rapid clearance, either due to rapid dissociation of the micelles and/or burst release of the drug. Particularly, it will be shown that by covalent inclusion of a series of polymerisable DMS or PTX prodrugs, the release rate of dexamethasone and paclitaxel respectively was truly controlled. Furthermore, this prodrug-loaded micelle complex had a real long blood circulation ($t_{1/2}$~14 h), a much prolonged period of therapeutic levels is obtained, and said complex was able to target subcutaneous tumour tissue in mice highly efficiently.

In accordance with the present invention, it is shown that drugs or other hydrophobic compounds benefit from the enhanced tumour accumulation of core-crosslinked micelles, when these were fixed inside the micelles via a biodegradable linker. This covalent conjugation creates a real tumour targeting carrier system, which is devoid of a burst release. When used in mice, the invention clearly demonstrates a therapeutic efficacy with regard to tumour regression and in a rheumatoid arthritis mouse model.

As said herein-above it is possible to control the release rate by tuning the sensitivity of the hydrolysable (ester) bond in the novel linker toward hydrolytic degradation. The exact type of linker used will determine the ultimate controlled release profile whereby the original, active, compound is released.

In addition, this strategy is broadly applicable to hydroxyl-, —COOH and —NH containing bioactive compounds.

The biodegradable character of the long-circulating cross-linked micelles themselves assures disintegration into small fragments that can be eliminated via renal clearance. In comparison with liposomes as the golden standard of nanoparticulate drug carriers, this drug delivery system of the invention leads to
(i) prolonged blood circulation—depot resulting in prolonged blood/tissue levels, e.g. taxol 6 hours, PTXLx(invention) up to 60 hours; and
(ii) higher accumulation in tissues with leaky vasculature, e.g. tumour and inflamed tissue. Passive accumulation at sites of increased capillary permeability increases the applicability of the micellar platform.

An additional attractive feature of the invention is the almost quantitative encapsulation efficiencies for a broad variety of hydrophobic compounds.

The present invention is not limited to polymeric micelles. Also other well known types of drug delivery vehicles such as polymer-drug conjugates can benefit from the present invention. It is within the scope of the skilled person to synthesise a suitable polymer-drug conjugate, and to entrap this within a range of possible drug delivery systems.

The polymeric micelle of the invention acts as a real carrier with sustained release profiles, and enhanced tissue accumulation and an embedded controlled release mechanism. This opens, besides selective drug delivery, many possibilities to carry out mechanistic studies to disentangle the order of pathophysiological circumstances and/or drug-interacting pathways of anti-cancer or inflammatory agents.

The controlled release system of the present invention is suitable for treatment of diseases including but not limited to diseases selected from the group consisting of cancer, infection, ophthalmological diseases, viral infection, bacterial infection, fungal infection, mucoplasma infection, parasite infection, inflammation, Dermatological diseases, Cardiovascular diseases, diseases of the central nerve system, autoimmune disease, proliferative diseases, arthritis, psychotic diseases, psoriasis, diabetes, metabolic disorders, lung diseases, respiratory diseases, pulmonary diseases, COPD, diseases of the muscoskeletal system, emphysema, edema, hormonal diseases. The controlled release system of the present invention is also suitable for delivery of anesthetics, to be used in vaccination, being either therapeutic or preventive.

In the working examples herein-below, use is made of the following materials:

Radiolabelled $^3$H-acetic anhydride and $^{14}$C-acetic anhydride were products of Amersham (Roosendaal, The Netherlands) and Perkin Elmer (Boston, USA), respectively. Ultima Gold liquid scintillation cocktail and Solvable tissue solubiliser were purchased from Perkin Elmer Bioscience BV (Groningen, The Netherlands). Dexamethasone (>98%), deuterated water ($D_2O$) and trifluoroacetic acid (TFA) were used as received from Sigma Aldrich (Zwijndrecht, The Netherlands). Dexamethasone-phosphate (DMS-P) was purchased at Bufa, Uitgeest, The Netherlands. Hydrogen peroxide and potassium persulphate (KPS) were both obtained from Merck (KGaA, Darmstadt, Germany). Paclitaxel (PTX, MP Biomedicals Inc, Illkirch, France), Taxol (Mayne Pharma, Brussels, Belgium), N,N,N',N'-tetramethylethylenediamine (TEMED, Fluka Chemie AG, Buchs, Switzerland), Acetonitril (ACN, Biosolve Ltd., Valkenswaard, The Netherlands) were all used as received. A 20% solution of sodium dodecyl sulphate (SDS) from Biorad Laboratories (Hercules, USA) was diluted 1:1 with buffer pH 5 (ammonium acetate, 120 mM). All buffers were filtered through 0.2 µm filters (Schleicher & Schuell MicroScience GmbH, Dassel, Germany) prior to use.

Further, in the working examples, the mean particle size ($Z_{ave}$) and polydispersity index (PD) of the micelles was determined with dynamic light scattering (DLS) using a Malvern ALV/CGS-3 Goniometer. $^1$H-NMR spectra were recorded with a Gemini 300 MHz spectrometer (Varian Associates Inc., NMR Instruments, Palo Alto, Calif., USA). Radioactivity of the micellar dispersions were determined in an Ultima Gold liquid scintillation cocktail and counted in a Packard Tricarb 2200 CA liquid scintillation counter.

EXAMPLE 1

Synthesis of the Linkers of the Present Invention

Drug linkers L1, L2 and L3, as exemplified in the table, herein-above, were synthesised according to the following routes:

11

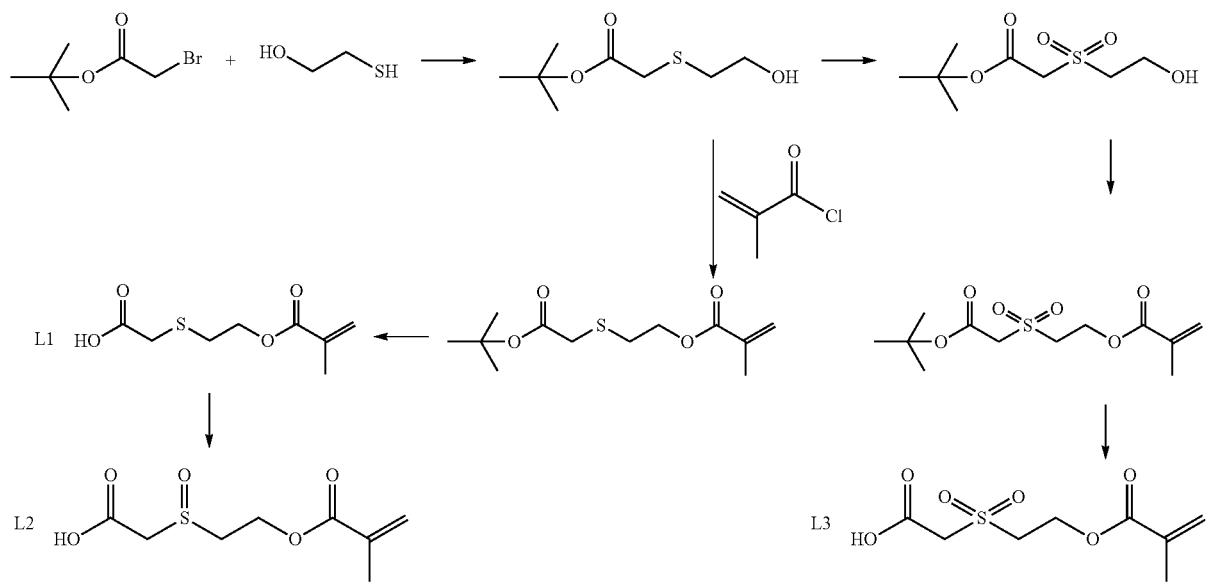

As to L1, in detail, the following steps were carried out:

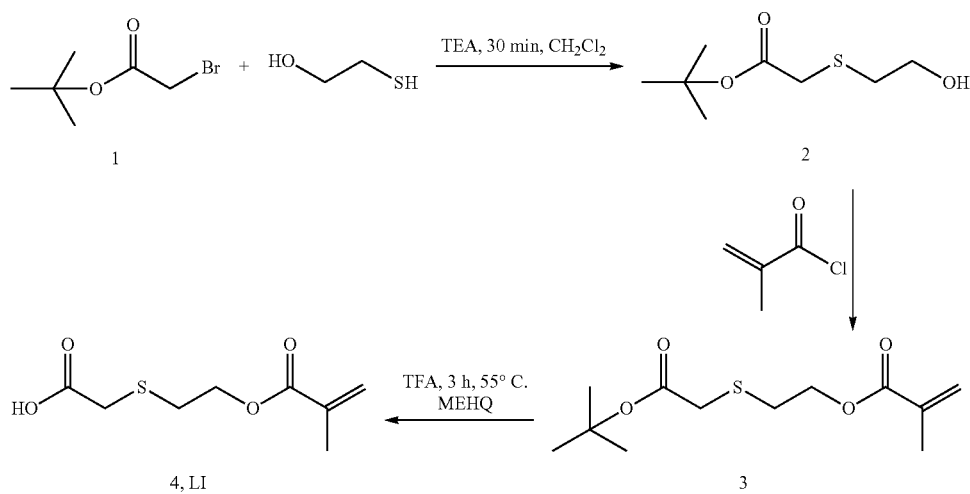

tert-butyl 2-(2-hydroxyethylthio)acetate (2):

tert-butyl bromoacetate 1 (15 g, 0.077 mol, 1 eqv.) and triethylamine (16 g, 0.16 mol, 2 eqv.) were dissolved in $CH_2Cl_2$ (100 mL) under nitrogen and cooled to 0 C. 2-mercaptoethanol (6.3 g, 0.081 mol, 1.05 eqv.) was slowly added to the mixture and the reaction mixture was warmed to room temperature. The reaction was stirred for 1 additional hour. Completion of the reaction was monitored by TLC (ethylacetate (EtOAc):hexane (Hex), 1:1 (v/v), Rf: 0.88). Base and acid extractions were carried out with 1M $KCO_3$, pH 10 and 1M NaOAc pH 3.5, twice, respectively. The combined organic layers were washed with brine, dried with $MgSO_4$ and filtered through Ø 185 mm whatman filter papers. The filtrate was concentrated in vacuo ($CH_2Cl_2$) to obtain 9.2 g (62% yield) 2 as a colourless oil.

$^1$H-NMR ($CDCl_3$): δ (ppm) 3.7 (q, 2H), 3.18 (s, 2H), 2.8 (d, 2H), 1.47 (s, 9H); $^1$H-NMR (DMSO): δ (ppm) 4.77 (s, OH), 3.52 (s, 2H), 3.19 (s, 2H), 2.62 (t, 2H), 1.39 (s, 9H)

12

2-(2-tert-butoxy-2-oxoethylthio)ethyl methacrylate (3)

2 (8.6 g, 0.045 mol, 1 eqv.) and triethylamine (9.05 g, 0.089 mol, 2 eqv.) were dissolved in $CH_2Cl_2$ (20 mL) on ice under nitrogen. Methacryloyl chloride (5.6 g, 0.054 mol, 1.2 eqv.) was added slowly to the mixture. The reaction mixture was warmed to room temperature and stirred for 2 hours. Completion of the reaction was confirmed by TLC (EtOAc:Hex, 1:1 (v/v), Rf: 0.86). Excess of methacryloyl chloride was removed by methanol to form methyl methacrylate. 3 was extracted twice with a saturated $NaHCO_3$ solution of pH=8. The combined organic layers were washed with brine and dried with $MgSO_4$ and filtered through Ø 185 mm whatman filter papers. The filtrate was concentrated in vacuo. Co-solvent evaporation with EtOAc, Hex and $CH_2Cl_2$, respectively, was performed to remove volatile impurities. 10.5 g (90% yield) 3 was obtained as a yellow oil.

$^1$H-NMR (CDCl$_3$): δ (ppm) 6.12 (s, H), 5.58 (s, H), 4.34 (t, 2H), 3.18 (s, 2H), 2.93 (t, 2H), 1.94 (s, 3H), 1.47 (s, 9H); $^{13}$C-NMR (CDCl$_3$): δ (ppm) 18.5 (CH$_3$), 28.2 (CH$_3$), 31.0 (CH$_2$), 35.1 (CH$_2$), 63.5 (CH$_2$), 81.9 (CH$_2$), 126.1 (C), 136.3 (C), 167.3 (C), 169.6 (C)

2-(2-(methacryloyloxy)ethylthio)acetic acid (4)

3 (2 g, 7.7 mmol, 1 eqv.) was slowly dissolved in trifluoroacetic acid (TFA) (10 mL) on ice under nitrogen. A trace amount of hydroquinone monomethyl ether (MEHQ) was added to the reaction mixture to prevent polymerisation. The reaction mixture was allowed to warm to room temperature and the reaction mixture was stirred for 2 hours at 55 C. Completion of the reaction was monitored by TLC(CHCl$_3$/MeOH/HOAc, 9:1:0.1 (v/v), Rf: 0.17). Excess of TFA was removed by evaporation and coevaporation with CH$_2$Cl$_2$ and the residue was purified on a silica gel column (Hex/EtOAc, 4:1 (v/v)). Pure 4 was dried with MgSO$_4$ and filtered through Ø 185 mm whatman filter papers. The filtrate was concentrated in vacuo. 1 g (63% yield) 4 was obtained as a light yellow oil.

$^1$H-NMR (CDCl$_3$): δ (ppm) 6.13 (s, 1H), 5.59 (s, 1H), 3.65 (t, 2H), 3.34 (s, 2H), 2.96 (t, 2H), 1.95 (s, 3H); $^1$H-NMR (DMSO): δ (ppm) 6.02 (s, 1H), 5.67 (s, 1H), 4.24 (t, 2H), 3.3 (s, 2H), 2.85 (t, 2H), 1.86 (s, 3H); $^{13}$C-NMR (DMSO): δ (ppm) 23.36 (CH$_3$), 35.69 (CH$_2$), 38.73 (CH$_2$), 68.68 (CH$_2$), 131.3 (CH$_2$), 141.1 (C), 171.9 (C), 176.8 (C)

As to L2, the following step was carried out:

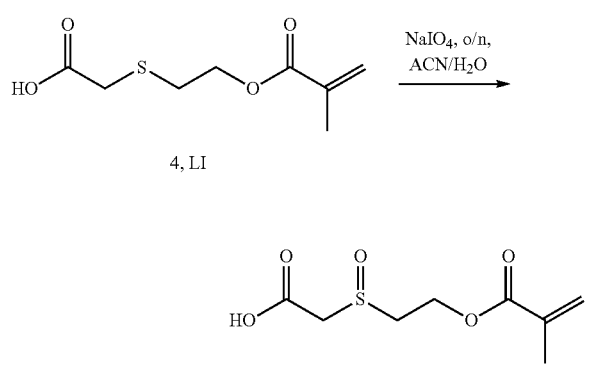

2-(2-(methacryloyloxy)ethylsulfinyl)acetic acid (5)

4 (1 g, 4.9 mmol, 1 eqv.) in acetonitrile (ACN) (10 mL) was mixed with a sodium periodate solution (1.1 g, 4.9 mmol, 1 eqv.) dissolved in H$_2$O (10 mL). The reaction mixture was stirred at RT overnight. The completion of the reaction was confirmed by TLC(CHCl$_3$/MeOH/TFA, 75:25:0.1 (v/v), Rf: 0.23). The reaction mixture was filtered via suction filtration to remove sodium iodate salts by EtOAc and dried with MgSO$_4$ and filtered through Ø 185 mm whatman filter papers. The filtrate was concentrated in vacuo and co-evaporated with CH$_2$Cl$_2$. 0.87 g (81% yield) 5 was obtained as a white solid.

$^1$H-NMR (CDCl$_3$): δ (ppm) 6.15 (s, 1H), 5.64 (s, 1H), 4.58 (m, 2H), 3.9 (d, 1H), 3.7 (d, 1H), 3.39 (m, 2H), 1.94 (s, 3H); $^1$H-NMR (DMSO): δ (ppm) 6.04 (s, 1H), 5.70 (s, 1H), 4.4 (m, 2H), 3.95 (d, 1H), 3.74 (d, H), 3.17 (m, 2H), 1.87 (s, 3H); $^{13}$C-NMR (DMSO): δ (ppm) 23.34 (CH$_3$), 55.38 (CH$_2$), 61.67 (CH$_2$), 62.83 (CH$_2$), 131.78 (CH$_2$), 140.96 (C), 171.64 (C), 172.93 (C)

As to L3, the following steps were carried out:

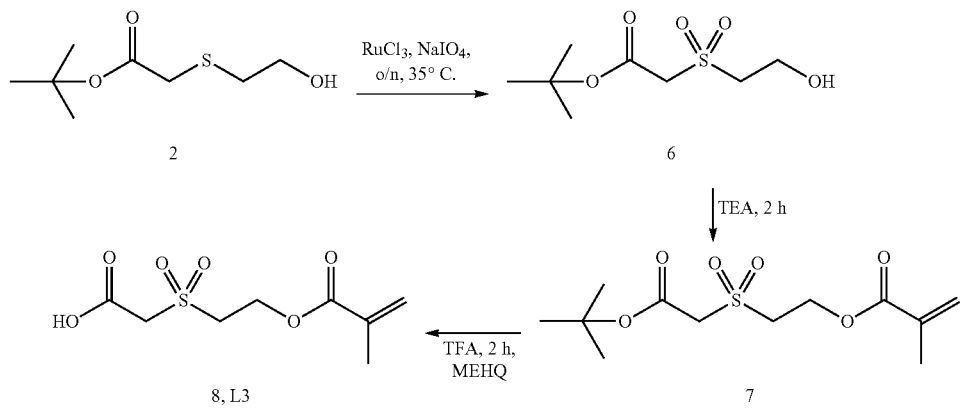

tert-butyl 2-(2-hydroxyethylsulfonyl)acetate (6)

2 (2.0 g, 10.4 mmol, 1 eqv.) was dissolved in ACN (20 mL) and CCl$_4$ (20 mL). A solution of NaIO$_4$ (6.7 g, 31 mmol, 3 eqv.) in 30 mL water was added to reaction mixture with vigorous stirring. RuCl$_3$ (43 mg, 0.21 mmol, 0.02 eqv.) was added once the two phases were mixed into an emulsion. The reaction mixture was then heated to 35 C and stirred overnight. The reaction was monitored via TLC (EtOAc/Hex, 3:2, Rf values: 6: 0.16, 2: 0.53). Once the reaction was complete, the reaction mixture was diluted with ether (100 mL), stirred vigorously for 15 minutes, dried with MgSO$_4$ and filtered through Ø 185 mm whatman filter papers. The residue was washed with ether (3×30 mL) and the filtrate concentrated in vacuo in a fume hood. This was later purified on a silica gel column (EtOAc/Hex, 3:2 (v/v)). 1.15 g (50% yield) 6 was obtained as a yellow oil.

$^1$H-NMR (DMSO): δ (ppm) 5.17 (s, OH), 4.22 (s, 2H), 3.80 (t, 2H), 3.37 (t, 2H), 1.42 (s, 9H)

2-(2-tert-butoxy-2-oxoethylsulfonyl)ethyl methacrylate (7)

Pure 6 (1 g, 4.6 mmol, 1 eqv.) was dissolved in dry dichloromethane (DCM) (10 mL) under nitrogen. Triethylamine (0.93 g, 9.2 mmol, 2 eqv.) and methacryloyl chloride (0.57 g, 5.5 mmol, 1.2 eqv.) were added to the reaction mixture on ice in the following order. The reaction mixture was allowed to warm to room temperature and was stirred for 3 hours. The completion of the reaction was confirmed by TLC (EtOAc/Hex, 3:2 (v/v), Rf values: 7: 0.69, 6: 0.27). Excess of methacryloyl chloride was removed with methanol to form methyl methacrylate. Base extraction (NaHCO$_3$, pH 8) was carried out twice. The reaction mixture was dried with MgSO$_4$ and filtered through Ø 185 mm whatman filter papers. The filtrate was concentrated in vacuo. The filtrate was purified on a silica gel column (100% EtOAc). 1.15 g (86% yield) 7 was obtained as an orange oil.

$^1$H-NMR (DMSO): δ (ppm) 6.06 (s, 1H), 5.71 (s, 1H), 4.48 (t, 2H), 4.29 (s, 2H), 3.69 (t, 2H), 1.87 (s, 3H), 1.42 (s, 9H)

2-(2-(methacryloyloxy)ethylsulfonyl)acetic acid (8)

Pure 7 (1.2 g, 3.9 mmol) was dissolved in TFA (15 mL) under nitrogen. A trace amount of MEHQ was added to the mixture and the reaction was stirred for 3 hours at 55° C. Completion of the reaction was confirmed by TLC (EtOAc/Hex/TFA: 60:40:0.1% (v/v), Rf: 0.38). The reaction mixture was purified on a silica gel column (EtOAc/Hex, 3/2). 0.6 g (65% yield) 8 was obtained as yellow oil.

$^1$H-NMR (DMSO): δ (ppm) 6.05 (s, 1H), 5.71 (s, 1H), 4.48 (t, 2H), 4.29 (s, 2H), 3.67 (t, 2H), 1.86 (s, 3H)

EXAMPLE 2

Synthesis of the Linker 2-(chlorocarbonyloxy)ethyl methacrylate (HEMA-chloroformate)

A solution of hydroxyethyl methacrylate (HEMA, 1.3 g, 10 mmol) and triethyl amine (1.1 g, 11 mmol) in 10 mL of chloroform was added dropwise to a stirred solution of phosgene (20% solution in toluene, 15.6 ml, 30 mmol) in 15 mL of chloroform at 0° C. The mixture was stirred for 1 hour at 0° C. and subsequently put under 50 mbar pressure to remove the excess of phosgene. After 30 min, the mixture was further concentrated under reduced pressure using a rotavap. The product was dissolved in 25 mL of THF and filtered to remove solid Et$_3$N.HCl. The THF was evaporated under reduced pressure and the residue was purified by Kugelrohr-distillation (90° C., 0.6 mmHg) affording the HEMA-chloroformate as a colourless oil (1.3 g, 67%).

EXAMPLE 3

Synthesis of Prodrugs

Dexamethasone and paclitaxel were used as model drug compounds. These hydrophobic drug molecules were derivatised with said linkers, thereby forming biodegradable prodrugs:

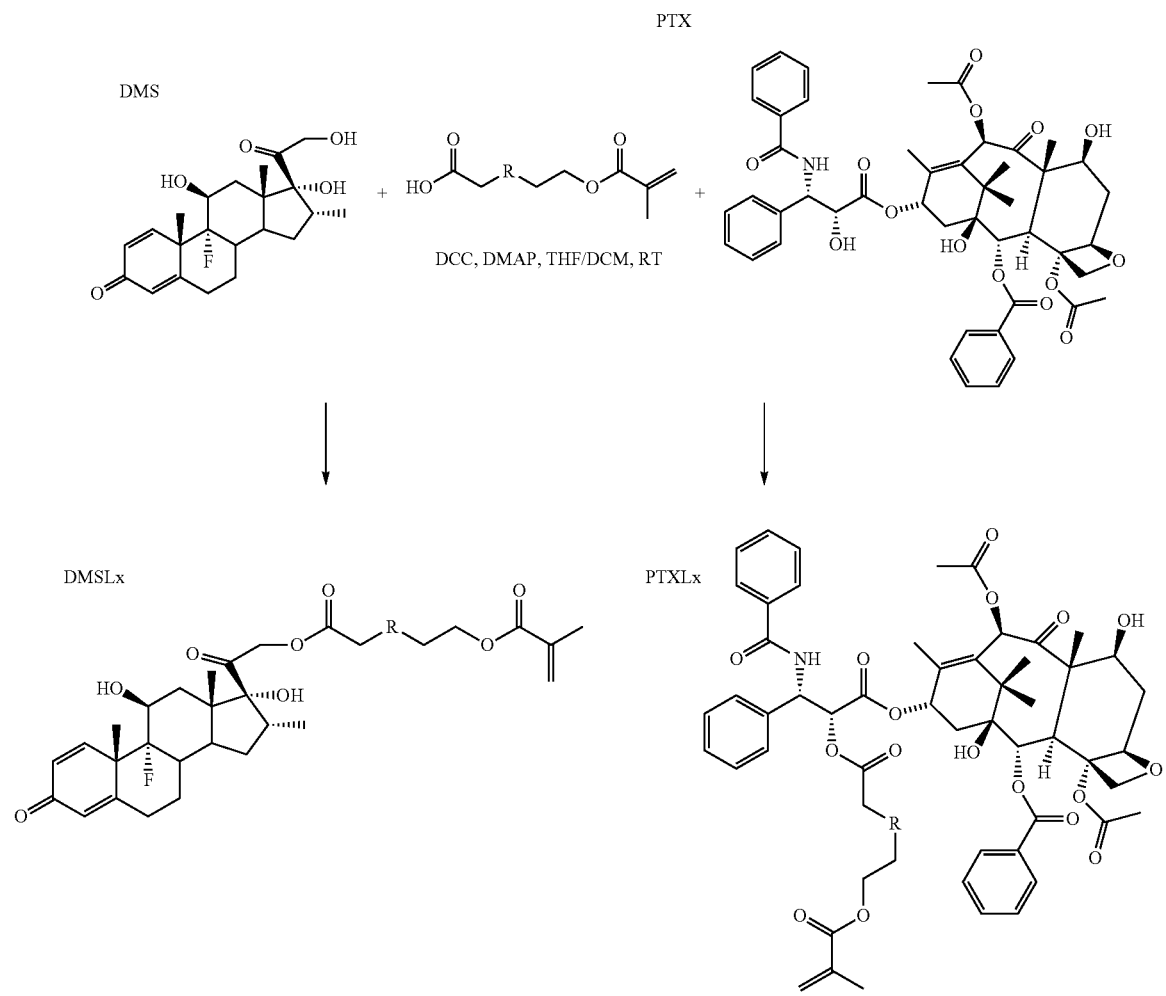

In this synthesis scheme, R is mono- or di-oxidized sulphur; i.e. linkers L1, L2 or L3.

2-(2-(2-((8S,9R,10S,11S,16R,17R)-9-fluoro-11,17-dihydroxy-10,13,16-trimethyl-3-oxo-6,7,8,9,10,11,12,13,14,15,16,17-dodecahydro-3H-cyclopenta[α]phenanthren-17-yl)-2-oxoethoxy)-2-oxoethylthio)ethyl methacrylate (DMSL1)

4 (0.25 g, 1.2 mmol, 1.05 eqv.) and 4-(dimethylamino)-pyridine (DMAP) (0.077 g, 0.63 mmol, 0.5 eqv.) were dissolved in dry $CH_2Cl_2$ (20 mL) under nitrogen. The reaction mixture was cooled on ice and N,N'-dicyclohexylcarbodiimide (DCC) (0.29 g, 1.4 mmol, 1.1 eqv.) was then added to the mixture together with DMS (0.5 g, 1.3 mmol, 1 eqv.) dissolved in dry THF (20 mL). The reaction was allowed to come to room temperature and after overnight stirring the completion of the reaction was confirmed by TLC (EtOAc/Hex, 3:2 (v/v), Rf: 0.76). Most of the solvent was evaporated and the remaining mixture was purified on a 15 cm silica gel column (EtOAc/Hex, 3:2 (v/v), Rf: 0.44). 0.5 gr (70% yield) DMSL1 was obtained as a white fluffy solid.

$^1$H-NMR (DMSO): δ (ppm) 7.26 (d, 1H), 6.22 (d, 1H), 6.02 (s, 1H), 5.98 (s, 1H*), 5.68 (s, 1H*), 5.39 (s, 1H), 5.19 (s, 1H), 5.18 (d, 1H), 4.82 (d, 1H), 4.27 (t, 2H*), 3.51 (s, 2H*), 2.91 (t, 2H*), 1.87 (s, 3H*), 1.46 (s, 3H), 0.86 (s, 3H), 0.78 (d, 3H); $^{13}$C-NMR (DMSO): δ (ppm) 20.54 ($CH_3$), 21.66 ($CH_3$), 23.42 ($CH_{3*}$), 28.44 ($CH_3$), 32.73 ($CH_2$), 35.61 ($CH_{2*}$), 35.7 ($CH_2$), 37.35 ($CH_2$), 38.02 ($CH_{2*}$), 39.19 (CH), 40.87 ($CH_2$), 41.09 (CH), 48.73 (CH), 53.42 ($CH_2$), 68.55 ($CH_{2*}$), 74.11 (CH), 75.68 (C), 76.16 (C), 95.93 ($CH_2$), 105.54 (CH), 107.85 (C), 129.52 (C), 131.43 ($CH_{2*}$), 134.41 (CH), 141.14 (C*), 158.15 (CH), 171.77 (C*), 172.46 (CH), 174.93 (C*), 190.68 (C); ESI-MS: $[M+H]^+$, calculated=579.69 d. found=578.85 d. $[2M+H]^+$, calculated=1158.38 d. found=1157.25 d.

2-(2-(2-((8S,9R,10S,11S,16R,17R)-9-fluoro-11,17-dihydroxy-10,13,16-trimethyl-3-oxo-6,7,8,9,10,11,12,13,14,15,16,17-dodecahydro-3H-cyclopenta[α]phenanthren-17-yl)-2-oxoethoxy)-2-oxoethylsulfinyl)ethyl methacrylate methacrylate (DMSL2)

5 (0.54 g, 2.4 mmol, 1.05 eqv.) was dissolved in dry THF (5 mL) and DMAP (0.14 g, 1.2 mmol, 0.5 eqv.) was added to the solution under nitrogen. After cooling on ice, a dexamethasone solution (0.91 g, 2.3 mmol, 1 eqv.) in dry THF (25 mL) and DCC (0.525 g, 2.5 mmol, 1.1 eqv.) were added to the mixture. The reaction mixture was slowly warmed to room temperature and stirred overnight at RT. The completion of the reaction was confirmed by TLC (EtOAc/Hex, 20:1 (v/v), Rf: 0.24). Most of the solvent was evaporated and the remaining solution was purified on a 20 cm silica gel column (EtOAc/Hex, 20:1 (v/v)). 1 g (73% yield) DMSL2 was obtained as a yellow fluffy solid.

$^1$H-NMR (DMSO): δ (ppm) 7.29 (d, 1H), 6.22 (d, 1H), 6.05 (s, 1H), 5.99 (s, 1H*), 5.71 (s, 1H*), 5.40 (d, 1H), 5.19 (s, OH), 5.18 (d, 1H), 4.88 (d, 1H), 4.5 (t, 2H*), 4.18 (s, 1H), 4.15 (d, 1H*), 4.00 (d, 1H*), 2.86 (s, 1H), 1.88 (s, 3H*), 1.47 (s, 3H), 0.87 (s, 3H), 0.78 (d, 3H); $^{13}$C-NMR (DMSO): δ (ppm) 20.51 ($CH_3$), 21.62 ($CH_3$), 23.32 ($CH_{3*}$), 28.34 ($CH_3$), 32.69 ($CH_2$), 35.68 ($CH_{2*}$), 35.84 ($CH_2$), 37.32 ($CH_2$), 39.80 (CH), 41.07 (CH), 48.72 (CH), 53.66 ($CH_2$), 55.53 ($CH_{2*}$), 61.67 ($CH_{2*}$), 62.72 ($CH_{2*}$), 74.11 (CH), 75.66 (C), 76.14 (C), 95.92 ($CH_2$), 105.54 (CH), 107.85 (C), 129.53 (C), 131.78 (CH*), 134.42 (CH), 140.94 (C*), 158.17 (CH), 170.98 (C*), 171.60 (CH*), 172.48 (C), 190.71 (C); ESI-MS: $[M+H]^+$, calculated=595.69 d. found=595.10 d. $[2M+H]^+$, calculated=1190.38 d. found=1189.65 d.

2-(2-(2-((8S,9R,10S,11S,16R,17R)-9-fluoro-11,17-dihydroxy-10,13,16-trimethyl-3-oxo-6,7,8,9,10,11,12,13,14,15,16,17-dodecahydro-3H-cyclopenta[α]phenanthren-17-yl)-2-oxoethoxy)-2-oxoethylsulfonyl)ethyl methacrylate (DMSL3)

8 (67 mg, 0.28 mmol, 1.05 eqv.) was dissolved in dry DCM (10 mL) and DMAP (0.017 g, 0.14 mmol, 0.5 eqv.) was added to the reaction mixture under nitrogen. Dexamethasone was dissolved (0.11 g, 0.27 mmol, 1 eqv.) in dry THF (10 mL). After cooling the mixture on ice DCC (0.21 g, 0.46 mmol, 1.1 eqv.) was added to the mixture together with dexamethasone. The reaction was stirred overnight at RT and the completion was confirmed by TLC (EtOAc/Hex, 7:3 (v/v), Rf: 0.47). Most of the solvent was evaporated and the remaining solution was purified on a 20 cm silica gel column (EtOAc/Hex, 7:3 (v/v)). 0.1 g (60% yield) DMSL3 was obtained as a white solid.

$^1$H-NMR (DMSO): δ (ppm) 7.29 (d, 1H), 6.22 (d, 1H), 6.05 (s, 1H), 5.99 (s, 1H*), 5.71 (s, 1H*), 5.40 (d, 1H), 5.19 (s, OH), 5.18 (d, 1H), 4.88 (d, 1H), 4.59 (s, 2H*), 4.51 (t, 2H*), 3.78 (t, 2H*), 1.87 (s, 3H*), 1.47 (s, 3H), 0.87 (s, 3H), 0.77 (d, 3H); $^{13}$C-NMR (DMSO): δ (ppm) ($CH_3$), ($CH_3$), 15.79 ($CH_3$), 16.93 ($CH_3$), 18.55 ($CH_2$), 23.63 ($CH_2$), 25.16 ($CH_2$), 27.98 ($CH_2$) 30.96 (CH), 32.59 (CH), 34.04 (CH), 36.36 ($CH_2$), 44.00 ($CH_2$), 48.75 ($CH_2$), 52.77 ($CH_2$), 58.24 (CH), 70.09 (C), 71.40 (C), 91.18 ($CH_2$), (CH), 124.80 (C), 127.25 (C), 129.69 (CH), 136.05 (CH), 153.42 (C), 163.23 (CH), 166.74 (C), 167.73 (CH), 185.96 (C), 204.66 (C); ESI-MS: $[M+H]^+$, calculated=611.69 d. found=611.05 d. $[2M+H]^+$, calculated=1222.38 d. found=1221.20 d.

The corresponding PTX based compounds were prepared by analogy.

Where desired, radioactive compounds $^3$H-dexamethasone (1 mCi/mL in ethanol) and $^{14}$C-paclitaxel ($^{14}$C-PTX) were obtained from Perkin Elmer (Boston, USA) and Campro Scientific BV (Veenendaal, The Netherlands), respectively. In the other cases, dexamethasone was obtained from Sigma Aldrich (Zwijndrecht, The Netherlands), and paclitaxel was obtained from MP Biomedicals Inc. (Illkirch, France).

EXAMPLE 4

Polymer synthesis

The used block copolymers were prepared as described by Rijcken et al., in Biomacromolecules, 2005. 6(4): p. 2343-2351 and in Biomaterials, 2007. 28(36): p. 5581-5593. The polymers contain a hydrophilic monomethoxy-PEG ($M_n$ of 5000 g/mol) block and a thermosensitive block composed of either the monolactate (36%) and dilactate (64%) of N-2-hydroxypropyl methacrylamide (HPMAm), or the monolactate (20%) and dilactate (80%) of N-2-hydroxyethyl methacrylamide (HEMAm). Subsequently, a fraction (10-15%) of the lactate side chains were methacrylated upon reaction with methacrylic anhydride as described previously in the Biomaterials reference. The molecular weight of the block copolymers and the critical micelle temperature was in all cases ~25 kDa and 8-12° C., respectively. $^3$H- and $^{14}$C-labelled methacrylated block copolymers were obtained using $^3$H- or $^{14}$C-acetic anhydride as described previously in the Biomaterials reference.

EXAMPLE 5

Preparation of Drug-Loaded Micelles

In general terms, and in typical experiments, block copolymers were based on PEG-b-poly(N-hydroxyalkyl methacrylamide-oligolactates) with partially methacrylated oligolactate units (thermosensitive polymer). More specifically, 2 types of polymer backbones were used: 2-hydroxypropyl-methacrylamide (HPMAm) and 2-hydroxyethylmethacrylamide (HEMAm). An aqueous solution of a thermosensitive block copolymer was mixed (typically 10:1 volume ratio) with a small amount of a concentrated solution of one of the prodrugs mentioned above in a water-miscible organic solvent (preferably with a low boiling temperature e.g. ethanol or tetrahydrofuran) at a temperature that does not allow micelle formation. Then, an initiator solution (KPS-TEMED, capable of producing free radicals, also other free radical initiators can be used) was added, immediately followed by rapid heating till above the critical micelle formation temperature (CMT). This resulted in the formation of monodisperse polymeric micelles where the prodrug was non covalently localised in the hydrophobic core via hydrophobic interactions. After micelle formation, a nitrogen atmosphere was created. Thereby, the initiator radicals induced polymerisation of the methacrylated polymers and the polymerisable prodrug compounds. This so-called crosslinking process resulted in the formation of an intertwined network and fixated the prodrug covalently inside the crosslinked micellar core (CCL PM).

DMS and DMS-prodrug-loaded micelles were prepared using the polymer based on HPMAm or HEMAm (both 14% % methacrylation). An ice-cold ammonium acetate buffered (pH 5) solution of polymer (8.3 volumes, dissolved overnight at 4° C.) was mixed with KPS (0.45 volume) and TEMED (0.25 volume). DMS (prodrugs) in ethanol (1 volume) was added, followed by rapid heating to 50° C. for 1 minute while vigorously stirring. The final concentrations of polymer, KPS, TEMED and drug were 20, 1.35, 3 and 2 mg/mL, respectively. The polymers constituting each micelle were subsequently crosslinked under a N-2-atmosphere for 1 hour at RT as described by Rijcken et al. in the above-cited article in Biomaterials. The KPS and TEMED concentrations were optimised to ensure complete methacrylate conversion (as described by Stenekes and Hennink in Polymer, 2000, 41(15), 5563-5569) without affecting the micellar morphology by premature polymerisation. Similarly, PTX and PTX-prodrugs loaded micelles were prepared.

DMS-P loaded liposomes were prepared as described previously (Banciu et al. J. Contr. Release, 2008, 127(2), 131-136; Schiffelers et al., Neoplasia, 2005, 7(2), 118-127). In brief, appropriate amounts of dipalmitoylphosphatidylcholine (Lipoid GmbH, Ludwigshafen, Germany), cholesterol (Sigma, St. Louis, USA), and polyethylene glycol 2000-distearoylphosphatidylethanolamine (Lipoid GmbH) in a molar ratio of 1.85:1.0:0.15, respectively, were dissolved in ethanol in a round-bottom flask. A lipid film was created by rotary evaporation. The film was hydrated with a solution of 100 mg/mL DMS-P. Liposome size was reduced by multiple extrusion steps through polycarbonate membranes (Nuclepore, Pleasanton, USA) with a final pore size of 50 nm. Mean particle size of the liposomes was determined by dynamic light scattering. Unencapsulated DMS-P was removed by dialysis in a Slide-A-Lyzer cassette with a molecular weight cut-off of 10 kDa at 4° C. with repeated changes of buffer. The aqueous phase after extraction was used for determining the glucocorticoid phosphate content by high performance liquid chromatography as described previously [8] and contained about 5 mg/mL DMS-P.

EXAMPLE 6

In Vitro Release Studies

DMS-prodrug-loaded HPMAm core-cross-linked (CCL) polymeric micelles (PM) (final concentration DMS 2 mg/mL) were at least ten-fold diluted in phosphate buffer containing 1% tween (pH 7.4, 150 mM) or borate buffer containing 1% tween (pH 8.4, 150 mM and pH 9.4 150 mM), and incubated at 37° C. The release of DMS was monitored by immediate analysis by UPLC detection on a Waters Acquity system and consisted of a BEH C18 column (1.7 m diameter, 50 mm length) at a column temperature of 50° C. The eluent was acetonitril/$H_2O$ (23:77, v/v) with a flow rate of 1 mL/min. The sample volume was 7.5 µL. UV detection occurred at 246 nm. The dexamethasone calibration curve was linear between 0.2 and 60 g/mL.

The DMS release curves from different prodrug CCL PM clearly demonstrated the large difference in release rate of DMS depending on the type of linker used (see FIG. 1).

DMS release followed by UPLC in time showed a clear linker dependent release rate, i.e. DMSL1 showed very slow release, while increasing the oxidation degree of the sulphur atom in the linker increased the release rate. The hydrolysis rate of a specific ester was pH-dependent in its turn, in that at pH 8.4 hydrolysis was accelerated as compared to the hydrolysis rate at pH 7.4. No release of DMS of the different DMS formulations was observed at pH 5 (data not shown). Moreover, the absence of a burst release indicates that the covalent entrapment of the dexamethasone prodrugs was in all cases complete. The same trend is consistently observed at different pH (i.e. 7.4 and 8.4) and for the different types of micelles (based on HPMAm and HEMAm).

It is hence shown that the oxidation state of the sulfur atom at the beta position of the ester bond can easily be varied, thereby yielding different linkers with varying degrees of hydrolytic stability. 50% release of DMS can for instance vary between ~1 week (DMSL3) and ~4 weeks (DMSL1) at physiological conditions.

Also, the release kinetics of PTX prodrug loaded HEMAm CCL PM were evaluated.

Figure 2:
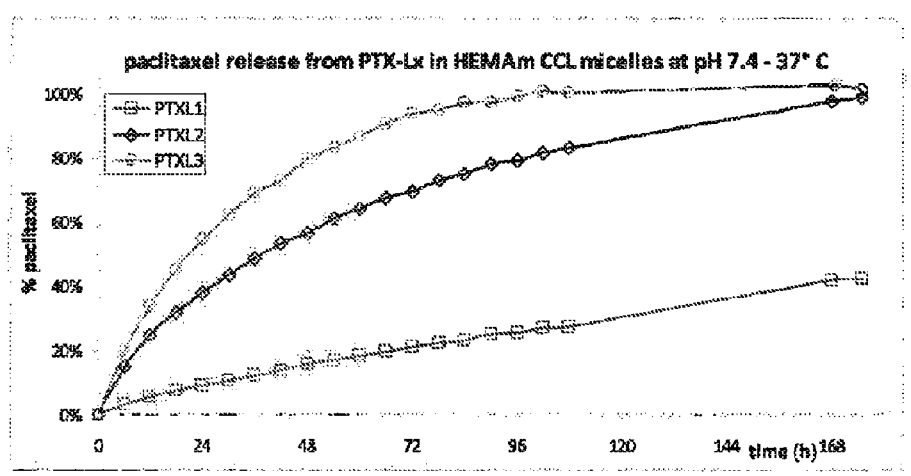
FIG. 2 is a graph showing the rate of release of paclitaxel from core-crosslinked micelles also as a function of the linker.

(FIG. 2; showing the PTX release kinetics of PTX prodrug loaded HEMAm CCL PM in buffer pH 7.4 at 37° C.).

The release of PTX from HEMAm CCL PM was also depending on the type of substituent used at the beta position of the ester bond. However, the overall release of PTX was much faster than the release kinetics of DMS. Clearly, atoms of the drug that are (near to the) conjugated (to the) linker also affected the ester bond sensitivity towards hydrolysis significantly.

Figure 3:
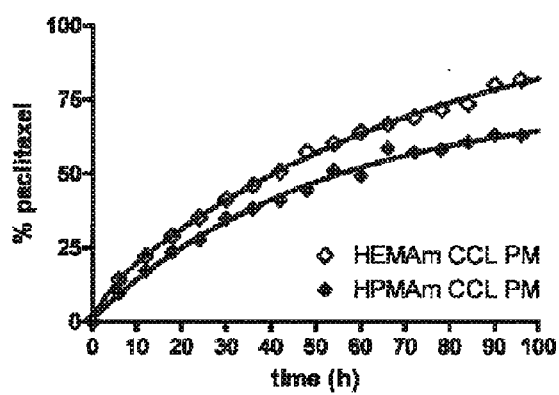
FIG. 3 is a graph showing the rate of paclitaxel released from core-crosslinked polymers as a function of the water content of the polymer resulting from the hydrophilicity of the polymer used.

Besides, as is apparent from FIG. 3 showing the PTX release kinetics of PTXL2 prodrug loaded HEMAm and HPMAm CCL PM in buffer pH 7.4 at 37° C. (each curve being the average of 4 independent measurements), the rate of linker hydrolysis is also slightly influenced by the hydrophilicity (water content) of the polymer, i.e. by the type of polymer used (either based on HPMAm or HEMAm). HEMAm is slightly more hydrophilic and, as a result, both the linker and the lactic acid side chains in poly(HEMAm-lactate) are more rapidly hydrolysed (see also WO/2005/087825). Moreover, the hydrolysis rate of the lactic acid side chains influences the rate of increase in hydrophilicity (and water uptake) of the micellar core.

Overall, these in vitro release studies clearly demonstrate the large difference in release kinetics of the original drug depending on the type of linker used and being secondary to the type of polymeric micelles and the type of drug evaluated.

EXAMPLE 7

Therapeutic Efficacy Study of DMSLx-Loaded Polymeric Micelles after i.v. Administration Tumour Model:

Mice bearing subcutaneous B16F10-melanoma tumours (see above) received an i.v. tail injection in case the tumour was between 100-200 mm$^3$. The dosage and formulations were 10 mg/kg of DMSL2 covalently entrapped in core-crosslinked HPMAm micelles, 10 mg/kg free DMS-P or saline (n=5-6 for each group). DMSL2-loaded micelles were prepared in pH 5 buffer as described above. Just before administration, the micellar solution was brought to pH 7.4 and an ionic strength of 300 mOsmolar with NaOH and NaCl, respectively. The tumour size was measured every day with a calliper and the body weight was also evaluated every day. Injections were repeated every 3 days up to the human end point of 2000 mm$^3$. In the control group, mice reached this end point already at day 6 after start of the treatment. In case of the DMSL2-loaded micelles, treatment was continued up to even 20 days, i.e. at least 6 injections.

Figure 4:
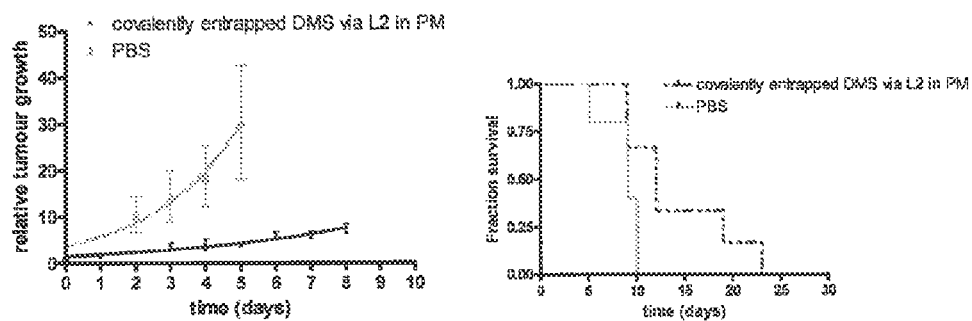
FIG. 4 is a pair of graphs showing the effect on tumor size in mice administered entrapped dexamethasone as compared to control mice and the survival rates of mice administered the entrapped dexamethasone as compared to control mice.

Particularly, for the therapeutic efficacy study, one of the formulations that showed a good in vitro release profile, i.e. DMSL2 co-crosslinked in the HPMAm micelles was compared with free DMS and PBS (FIG. 4; showing the relative tumour growth rates (left) and animal survival (right) of DMSL2 co-cross-linked in HPMAm micelles, upon multiple (3-day interval) i.v. administrations in B16F10 tumour bearing mice)

According to the Kaplan Meier analysis (FIG. 4, right), DMSL2 micelles had a significant (p=0.041) therapeutic effect compared to PBS. There is also a tendency towards a higher efficacy as compared to free DMS-P, but this is not that significant (FIG. 4, left). Despite the frequent administration of the micellar formulation (up to 6 times), no indications of any local or systems toxicity was observed. In addition, no loss of body weight was seen upon the daily measurements.

Figure 5:
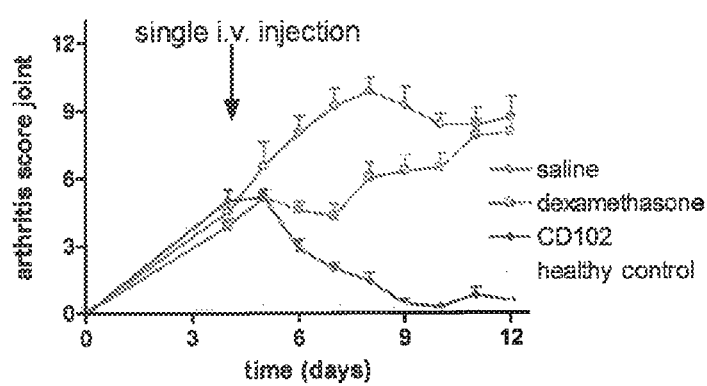
FIG. 5 shows the effect of administering entrapped dexamethasone by intravenous injection into arthritic mice.

RA Model:

To mice with a collagen antibody induced arthritis in their knee joint, a single i.v. injection of 10 mg DMS/kg was given, either as free drug or as DMSL3 (CD102) As placebo, saline was i.v. injected and the healthy, non-affect joint was taken as control. The results clearly indicate that upon intravenous injection, only the DMSL3 PM resulted in significant (almost complete) suppression of the arthritis symptoms (here joint swelling). This indicates the superior pharmacokinetic behavior (release rate over prolonged period and enhanced accumulation in inflamed tissue) as compared to free dexamethasone. The results are shown in FIG. 5.

EXAMPLE 8

PK and Therapeutic Efficacy Study of PTXLx-Loaded Polymeric Micelles after i.v. Administration In in vivo pharmacokinetic studies, paclitaxel blood levels after intravenous administration of PTXL2 PM formulations (~10 mg/kg paclitaxel) were determined in a therapeutic efficacy study against subcutaneous B16F10 tumour bearing mice with taxol and PBS as control. See in this light, the following Table:

| formulation | t = 24 u | t = 48 u |
|---|---|---|
| Taxol | below LOQ | below LOQ |
| PTXL2 HEMAm | 4027 ng/mL free PTX | 100 ng/mL free PTX |
| PTXL2 HPMAm | 3965 ng/mL free PTX | 125 ng/mL free PTX |

Particularly, this Table shows paclitaxel blood levels after intravenous administration of taxol or PTXL2-prodrug CCL PM formulations to subcutaneous B16F10 tumour bearing mice (as determined by LC-MS, limit of quantification (LOQ)<10.3 ng/mL, n being 3-5). These pharmacokinetic data of free paclitaxel indicated the long blood residence of the PTX prodrugs loaded CCL PM and the controlled release of PTX.

Healthy Mice i.v.

PTXL1, PTXL2 and PTXL3 micelles were iv administered at a dose of 12.5 mg/kg to mice, as PTX (3 animals/sampling time). As controls, also taxol and Abraxane were administered as control as being the current commercial paclitaxel formulations. Blood samples and various organs (liver, spleen) were collected at different time points after injection.

Figure 6A:
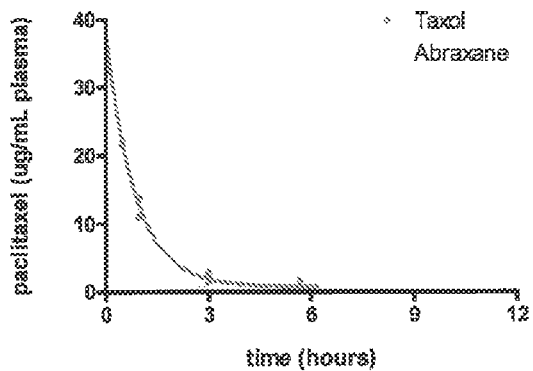
FIGS. 6a, 6b and 6c are graphs of pharmacokinetics of paclitaxel coupled to core-crosslinked polymers using various linkers as compared to blood levels of paclitaxel administered alone.
Figure 6B:
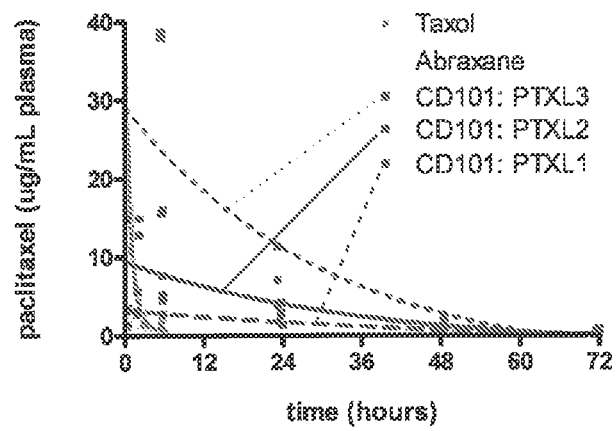

In FIGS. 6a and b all curves correspond to released paclitaxel.

Figure 6C:
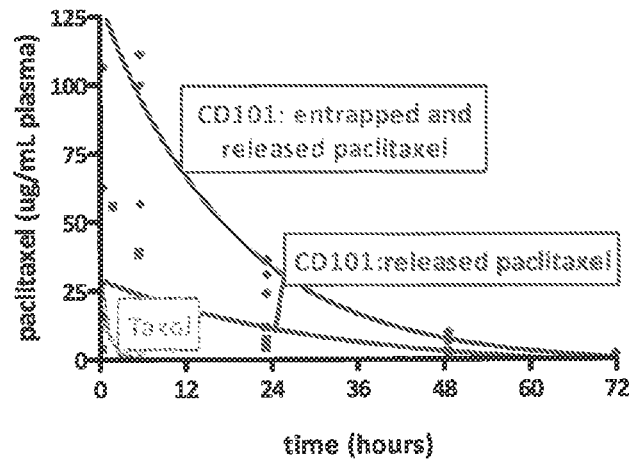

When also conserving the paclitaxel entrapped micelle, in case of PTXL3 the blood pattern was observed as shown in FIG. 6c.

The entrapped and released paclitaxel clearly indicates the long-circulating profile of the PTXLx micelles, which in turn also indicates that paclitaxel is protected from degradation while in the micelles.

| Name | average free PTX to total PTX | AUC total | AUC free |
|---|---|---|---|
| PTXL1 | 4% | 2275 | 96 |
| PTXL2 | 15% | 1367 | 227 |
| PTXL3 | 24% | 2328 | 683 |
| Taxol | n.a. | n.a. | 28 |
| Abraxane | n.a. | n.a. | 5 |

The above table shows a clear indication of the prolonged blood circulation as compared to current commercial formulations. Next, the tuneable release rate is observed, with minimal amount of paclitaxel in case of the slow-releasing PTXL1 and the highest amount of released paclitaxel in case of the (so-far) fastest-releasing PTXL3.

Healthy Mice i.p. And s.c.

Similarly, PTX11 micelles are also administered subcutaneously and intraperitoneally, resulting in blood levels, where the paclitaxel is also controlled release in time. This indicates that the release mechanism is really generic, even upon other different routes of administration.

Healthy Rats—i.v. Injection

Figure 7:
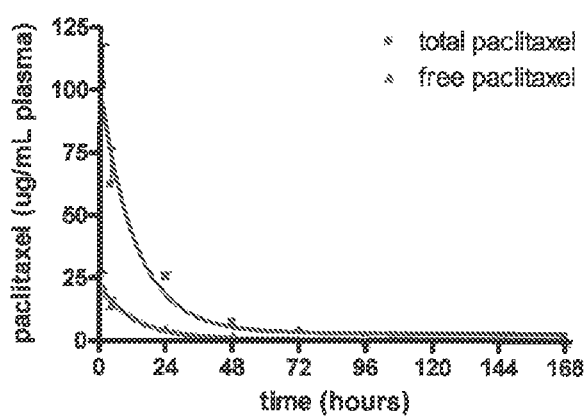
FIG. 7 shows levels of paclitaxel both free and entrapped as a function of time for subcutaneous and intraperitoneal administration.

The pattern shown in FIG. 7 was observed upon i.v. injection of PTXL2 micelles.

The most important results and conclusions are the: long blood circulation profile; and that the % released paclitaxel in blood equals to the % released in mice: that is, equal release mechanisms are observed.

Most importantly with regard to use of these linkers in various embodiments, this new type of linker molecules appeared to be fully safe in various preclinical toxicity studies, upon single or repeated administration to mice and rats. Next, even upon increasing dosages, no local or systemic effects were observed, thereby indicating that these type of linkers nor their biodegradable fragments cause any noticeable side effects.

The invention claimed is:

1. A compound comprising a linker of the formula (1) or (2):

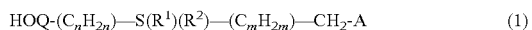

$$\text{HOQ-}(C_nH_{2n})\text{—S}(R^1)(R^2)\text{—}(C_mH_{2m})\text{—CH}_2\text{-A} \quad (1)$$

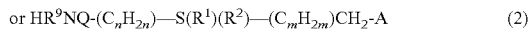

$$\text{or HR}^9\text{NQ-}(C_nH_{2n})\text{—S}(R^1)(R^2)\text{—}(C_mH_{2m})\text{CH}_2\text{-A} \quad (2)$$

wherein $R^9$ is H or $C_1$-$C_3$ alkyl
wherein n and m are integers from 0 to 20;
wherein each of $R^1$ and $R^2$ is independently an electron lone pair, =O or =N—$R^X$, wherein each $R^X$ is independently selected from the group consisting of H;
straight or branched $C_1$-$C_6$ alkyl, optionally substituted by one or more substituents selected from the group consisting of halogen, hydroxyl, amino, amino substituted by one or two $C_1$-$C_3$ alkyl, carboxylic acid, nitro and cyano;
straight or branched $C_2$-$C_6$ alkenyl, optionally substituted by one or more substituents selected from the group consisting of halogen, hydroxyl, amino, amino substituted by one or two $C_1$-$C_3$ alkyl, carboxylic acid, nitro and cyano;
an aromatic moiety, optionally substituted by one or more substituents selected from the group consisting of halogen, hydroxyl, amino, amino substituted by one or two $C_1$-$C_3$ alkyl, carboxylic acid, nitro and cyano;
halogen, hydroxyl, amino, amino substituted with one or two $C_1$-$C_3$ alkyl, carboxylic acid, nitro and cyano;
wherein A is a polymerisable moiety —$P^L$—$R^VC$=$CR^UR^W$, wherein $P^L$ is a linking group —O—, —NH—, —N— substituted with a $C_1$-$C_3$ alkyl, or $P^L$ is —O—C(O)— or —O—(C(O))$_r$—$C_bH_{2b}$—, wherein r is 0 or 1 and b is 1-6; and each $R^U$, $R^V$ and $R^W$ is independently hydrogen or a $C_1$-$C_3$ alkyl group; and
wherein Q is a direct bond or a C=O, a C=NH or a C=$NR^P$ group wherein $R^P$ is a $C_1$-$C_3$ alkyl group,
wherein said linker is coupled covalently to a bioactive molecule,
wherein the bioactive molecule is a drug molecule, a peptide, a protein, an imaging agent, a gene construct or a combination thereof; and
wherein the bioactive molecule is coupled through a -QOH or -QNR$^9$H group of said linker of formula (1) or (2).

2. The compound of claim 1, wherein the bioactive molecule is a glucocorticosteroid.

3. The compound of claim 1, wherein the bioactive molecule is a chemostatic agent.

4. A drug delivery system which comprises an intertwined polymer matrix entrapping a bioactive molecule, wherein the bioactive molecule is covalently linked to the polymer matrix through a linker of formula (1) or (2):

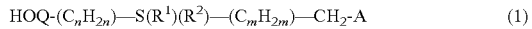

$$\text{HOQ-}(C_nH_{2n})\text{—S}(R^1)(R^2)\text{—}(C_mH_{2m})\text{—CH}_2\text{-A} \quad (1)$$

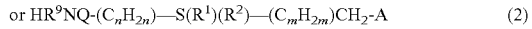

$$\text{or HR}^9\text{NQ-}(C_nH_{2n})\text{—S}(R^1)(R^2)\text{—}(C_mH_{2m})\text{CH}_2\text{-A} \quad (2)$$

wherein $R^9$ is H or $C_1$-$C_3$ alkyl
wherein n and m are integers from 0 to 20;
wherein each of $R^1$ and $R^2$ is independently an electron lone pair, =O or =N—$R^X$, wherein each $R^X$ is independently selected from the group consisting of H;
straight or branched $C_1$-$C_6$ alkyl, optionally substituted by one or more substituents selected from the group consisting of halogen, hydroxyl, amino, amino substituted by one or two $C_1$-$C_3$ alkyl, carboxylic acid, nitro and cyano;
straight or branched $C_2$-$C_6$ alkenyl, optionally substituted by one or more substituents selected from the group consisting of halogen, hydroxyl, amino, amino substituted by one or two $C_1$-$C_3$ alkyl, carboxylic acid, nitro and cyano;
an aromatic moiety, optionally substituted by one or more substituents selected from the group consisting of halogen, hydroxyl, amino, amino substituted by one or two $C_1$-$C_3$ alkyl, carboxylic acid, nitro and cyano;
halogen, hydroxyl, amino, amino substituted with one or two $C_1$-$C_3$ alkyl, carboxylic acid, nitro and cyano;
wherein A is a polymerisable moiety —$P^L$—$R^VCR^UR^W$, wherein $P^L$ is a linking group —O—, —NH—, —N— substituted with a $C_1$-$C_3$ alkyl, or $P^L$ is —O—C(O)— or —O—(C(O))$_r$—$C_bH_{2b}$—, wherein r is 0 or 1 and b is 1-6; and each $R^U$, $R^V$ and $R^W$ is independently hydrogen or a $C_1$-$C_3$ alkyl group; and
wherein Q is a direct bond or a C=O, a C=NH or a C=$NR^P$ group wherein $R^P$ is a $C_1$-$C_3$ alkyl group;
wherein the bioactive molecule is a drug molecule, a peptide, a protein, an imaging agent, a gene construct or a combination thereof; and
wherein the bioactive molecule is coupled through a -QOH or -QNR$^9$H group of said linker of formula (1) or (2).

5. The drug delivery system of claim 4, wherein the bioactive molecule is a drug molecule which is a glucocorticosteroid or a chemotherapeutic agent.

6. A method of delivering a glucocorticosteroid or a chemostatic agent to a subject in need thereof, comprising administering to the subject the drug delivery system of claim 5.

7. The compound of claim 2, wherein the glucocorticosteroid is dexamethasone.

8. The compound of claim 3, wherein the chemostatic agent is paclitaxel.

9. The drug delivery system of claim 5, wherein the glucocorticosteroid is dexamethasone and the chemotherapeutic agent is paclitaxel.

10. The drug delivery system of claim 4 wherein the intertwined polymer matrix is in the form of a nanoparticle, a micelle, a microsphere, a hydrogel or a coating.

11. A compound comprising a linker of the formula (1) or (2):

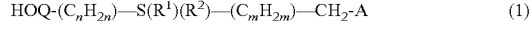

$$\text{HOQ-}(C_nH_{2n})\text{—S}(R^1)(R^2)\text{—}(C_mH_{2m})\text{—CH}_2\text{-A} \quad (1)$$

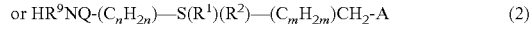

$$\text{or HR}^9\text{NQ-}(C_nH_{2n})\text{—S}(R^1)(R^2)\text{—}(C_mH_{2m})\text{CH}_2\text{-A} \quad (2)$$

wherein $R^9$ is H or $C_1$-$C_3$ alkyl
wherein n and m are integers from 0 to 20;
wherein each of $R^1$ and $R^2$ is independently an electron lone pair, =O or =N—$R^X$, wherein each $R^X$ is independently selected from the group consisting of H;
straight or branched $C_1$-$C_6$ alkyl, optionally substituted by one or more substituents selected from the group consisting of halogen, hydroxyl, amino, amino substituted by one or two $C_1$-$C_3$ alkyl, carboxylic acid, nitro and cyano;
straight or branched $C_2$-$C_6$ alkenyl, optionally substituted by one or more substituents selected from the group consisting of halogen, hydroxyl, amino, amino substituted by one or two $C_1$-$C_3$ alkyl, carboxylic acid, nitro and cyano;

an aromatic moiety, optionally substituted by one or more substituents selected from the group consisting of halogen, hydroxyl, amino, amino substituted by one or two $C_1$-$C_3$ alkyl, carboxylic acid, nitro and cyano;

halogen, hydroxyl, amino, amino substituted with one or two $C_1$-$C_3$ alkyl, carboxylic acid, nitro and cyano;

wherein A is a polymerisable moiety —$P^L$—$R^V CR^U R^W$, wherein $P^L$ is a linking group —O—, —NH—, —N— substituted with a $C_1$-$C_3$ alkyl, or $P^L$ is —O—C(O)— or —O—(C(O))$_r$—$C_b H_{2b}$—, wherein r is 0 or 1 and b is 1-6; and each $R^U$, $R^V$ and $R^W$ is independently hydrogen or a $C_1$-$C_3$ alkyl group; and wherein Q is a direct bond or a C=O, a C=NH or a C=$NR^P$ group wherein $R^P$ is a $C_1$-$C_3$ alkyl group, wherein said linker is coupled covalently to a building block, which building block assembles into an intertwined polymer matrix, wherein the building block is coupled through a -QOH or -QNR$^9$H group of said linker of formula (1) or (2).

12. The compound of claim 11 wherein the intertwined polymer matrix is in the form of a nanoparticle, a micelle, a microsphere, a hydrogel or a coating.

13. A method of delivering a bioactive molecule to a subject in need thereof, comprising administering to the subject the drug delivery system of claim 4.

14. The compound of claim 11 wherein the building block is PEGylated HPMAm oligolactate or PEGylated HEMA oligolactate.

* * * * *